(12) United States Patent
Lura et al.

(10) Patent No.: US 10,493,192 B2
(45) Date of Patent: Dec. 3, 2019

(54) INFUSATE SLEEVE

(71) Applicant: Medtronic, Inc., Minneapolis, MN (US)

(72) Inventors: David B. Lura, Maple Grove, MN (US); Bartosz Korec, Palm Harbor, FL (US); Yue Qiang Xue, Shanghai (CN); Jin Huang, Shanghai (CN)

(73) Assignee: Medtronic, Inc., Minneapolis, MN (US)

( * ) Notice: Subject to any disclaimer, the term of this patent is extended or adjusted under 35 U.S.C. 154(b) by 124 days.

(21) Appl. No.: 15/593,539

(22) Filed: May 12, 2017

(65) Prior Publication Data

US 2018/0326139 A1 Nov. 15, 2018

(51) Int. Cl.
*A61M 1/16* (2006.01)
*A61K 33/14* (2006.01)
*A61K 33/10* (2006.01)
*A61M 1/36* (2006.01)

(52) U.S. Cl.
CPC ........... *A61M 1/1666* (2014.02); *A61K 33/10* (2013.01); *A61K 33/14* (2013.01); *A61M 1/1668* (2014.02); *A61M 1/3643* (2013.01); *A61M 2205/7545* (2013.01); *A61M 2209/084* (2013.01)

(58) Field of Classification Search
CPC .................................................. A61M 1/1666
See application file for complete search history.

(56) References Cited

U.S. PATENT DOCUMENTS

| 4,747,822 | A | 5/1988 | Peabody |
| 4,950,230 | A | 8/1990 | Kendell |
| 5,032,265 | A | 7/1991 | Jha |
| 5,141,493 | A | 8/1992 | Jacobsen |
| 5,643,201 | A | 7/1997 | Peabody |
| 5,794,669 | A * | 8/1998 | Polaschegg ......... A61M 1/1656 141/100 |
| 5,972,223 | A * | 10/1999 | Jonsson ................ A61L 2/0023 137/88 |
| 2010/0069817 | A1 | 3/2010 | Falkvall |
| 2010/0078092 | A1 | 4/2010 | Weilhoefer |
| 2010/0312172 | A1 | 12/2010 | Hoffman |
| 2012/0199205 | A1 | 8/2012 | Eyrard |
| 2013/0001165 | A1 | 1/2013 | Pohlmeier |
| 2013/0015302 | A1 | 1/2013 | Gkhan rter |

(Continued)

FOREIGN PATENT DOCUMENTS

| CN | 202105667 | 1/2012 |
| DE | 202014104252 | 12/2015 |

(Continued)

OTHER PUBLICATIONS

PCTUS2017025858 International Search Report dated Jun. 29, 2017.

(Continued)

*Primary Examiner* — Patrick J Orme

(74) *Attorney, Agent, or Firm* — Kenneth Collier

(57) ABSTRACT

The invention relates to infusate sleeves for use in dialysis and related systems and methods. The infusate sleeves include a sleeve body, a filter inside of the sleeve body, a rigid disk covering an opening in the top of the sleeve body, a draw tube connected to the rigid disk and extending downwardly into the sleeve body, and a fluid connector fluidly connected to the draw tube for connection to a dialysis system.

20 Claims, 11 Drawing Sheets

(56) References Cited

U.S. PATENT DOCUMENTS

| | | |
|---|---|---|
| 2013/0062265 A1 | 3/2013 | Balschat |
| 2014/0018727 A1 | 1/2014 | Burbank |
| 2014/0217029 A1 | 8/2014 | Meyer |
| 2014/0238940 A1 | 8/2014 | Schwarz |
| 2017/0021076 A1 | 1/2017 | Lura |
| 2017/0021086 A1 | 1/2017 | Lura |

FOREIGN PATENT DOCUMENTS

| | | |
|---|---|---|
| EP | 0714668 | 6/1996 |
| JP | 2006325668 A | 12/2006 |
| WO | WO2000057935 A1 | 10/2000 |
| WO | 2011113572 A1 | 9/2011 |
| WO | 2012138604 A2 | 10/2012 |
| WO | WO 2013077844 | 5/2013 |
| WO | 2014121158 A1 | 8/2014 |
| WO | 2015071247 A1 | 5/2015 |
| WO | WO 2017004449 | 1/2017 |

OTHER PUBLICATIONS

PCTUS2017025876 International Search Report dated Jun. 29, 2017.
PCTUS2017025876 Written Opinion dated Jun. 29, 2017.
Written Opinion, Application PCT/2016/043948, dated Feb. 2, 2017.
Written Opinion, Application PCT/US2016/043935, dated Feb. 2, 2017.

* cited by examiner

INFUSATE SLEEVE

FIELD OF THE INVENTION

The invention relates to infusate sleeves for use in dialysis and related systems and methods. The infusate sleeves include a sleeve body, a filter inside of the sleeve body, a rigid disk covering an opening in the top of the sleeve body, a draw tube connected to the rigid disk and extending downwardly into the sleeve body, and a fluid connector fluidly connected to the draw tube for connection to a dialysis system.

BACKGROUND

During priming of a dialysis system and during dialysis treatment, specific concentrations of specific solutions, such as sodium chloride, sodium bicarbonate, and cation infusates, must be added to the dialysate flow path. Further, many cations, such as potassium, calcium and magnesium, can cross the dialyzer and be removed from a patient during dialysis. The cations must be added back into the dialysate to maintain the concentration of the cations at a desired level. Sodium bicarbonate can be used during dialysis as a buffer to control the pH of the dialysate and to treat acidosis by delivering bicarbonate across the dialysis membrane to the patient receiving a treatment. Because the relative concentrations of the sodium chloride, sodium bicarbonate, and cations can vary from patient to patient or when used for either priming or treatment, each of the solutions must be added from separate containers. Before each use, the separate containers must be cleaned and sterilized driving up costs and time.

There is a need for systems and methods that can use inexpensive disposable components within reusable containers for holding each of the substances to be added to a dialysate flow path during either treatment or priming. There is a need for the disposable components that allow solid infusate sources to be dissolved, creating infusate solutions of known concentration while preventing any particulate matter from entering the dialysis system.

SUMMARY OF THE INVENTION

The first aspect of the invention relates to an infusate sleeve. In any embodiment of the first aspect of the invention, the infusate sleeve can include a sleeve body; a filter inside of the sleeve body and sealed to the sleeve body separating the sleeve body into a top portion and a bottom portion; a rigid disk sealed to a top portion of the sleeve body; the rigid disk covering an opening in the top portion of the sleeve body; a draw tube connected to the rigid disk; the draw tube downwardly extending from the rigid disk through the filter; and a fluid connector connected to an outside of the rigid disk; the fluid connector in fluid connection with the draw tube.

In any embodiment, the filter and rigid disk can be heat sealed to the sleeve body.

In any embodiment, the sleeve body can be flexible.

In any embodiment, the sleeve body can be rigid.

In any embodiment, the fluid connector can be a bi-channel connector.

In any embodiment, a first channel in the bi-channel connector can be fluidly connected to the draw tube.

In any embodiment, the sleeve body can have an opening in the bottom portion of the sleeve body; and the infusate sleeve can include a cup covering the opening in the bottom portion of the sleeve body; the cup sealed to the sleeve body.

In any embodiment, the filter can be sealed to the cup.

Any of the features disclosed as being part of the first aspect of the invention can be included in the first aspect of the invention, either alone or in combination.

The second aspect of the invention is drawn to an infusate container. In any embodiment, the infusate container can include an infusate container body; the infusate sleeve of the first aspect of the invention inside the container body; and a cap; wherein the fluid connector extends through an opening in the cap.

In any embodiment, the infusate sleeve can be flexible.

In any embodiment, the infusate sleeve can be rigid.

Any of the features disclosed as being part of the second aspect of the invention can be included in the second aspect of the invention, either alone or in combination.

The third aspect of the invention is drawn to a dialysis system. In any embodiment, the dialysis system can include a dialysate flow path; one or more fluid connectors fluidly connecting one or more infusate containers of the second aspect of the invention to the dialysate flow path; and at least one pump connected to a fluid line fluidly connected to the fluid connectors.

In any embodiment, the fluid connector can be a bi-channel connector.

In any embodiment, a first channel of the bi-channel connector can fluidly connect the draw tube to a first fluid line; and a second channel of the bi-channel connector can fluidly connect the infusate sleeve to a second fluid line.

In any embodiment, the infusate sleeve can contain sodium chloride, sodium bicarbonate, a cation infusate, or combinations thereof.

Any of the features disclosed as being part of the third aspect of the invention can be included in the third aspect of the invention, either alone or in combination.

The fourth aspect of the invention is drawn to a method. In any embodiment, the method can include the steps of flowing water into an infusate container the second aspect of the invention, wherein the infusate container contains a solid infusate; dissolving at least a portion of the solid infusate to make an infusate solution; and flowing the infusate solution into a dialysate flow path.

In any embodiment, the step of flowing water into the infusate container can include flowing water through a first channel of a bi-channel connector; and the step of flowing the infusate solution into the dialysate flow path can include flowing the infusate solution through a second channel of the bi-channel connector.

In any embodiment, the step of dissolving at least a portion of the solid infusate to make an infusate solution can include making a saturated infusate solution.

In any embodiment, the infusate can be sodium bicarbonate, sodium chloride, a cation infusate, or a combination thereof.

DETAILED DESCRIPTION OF THE INVENTION

Figure 1:
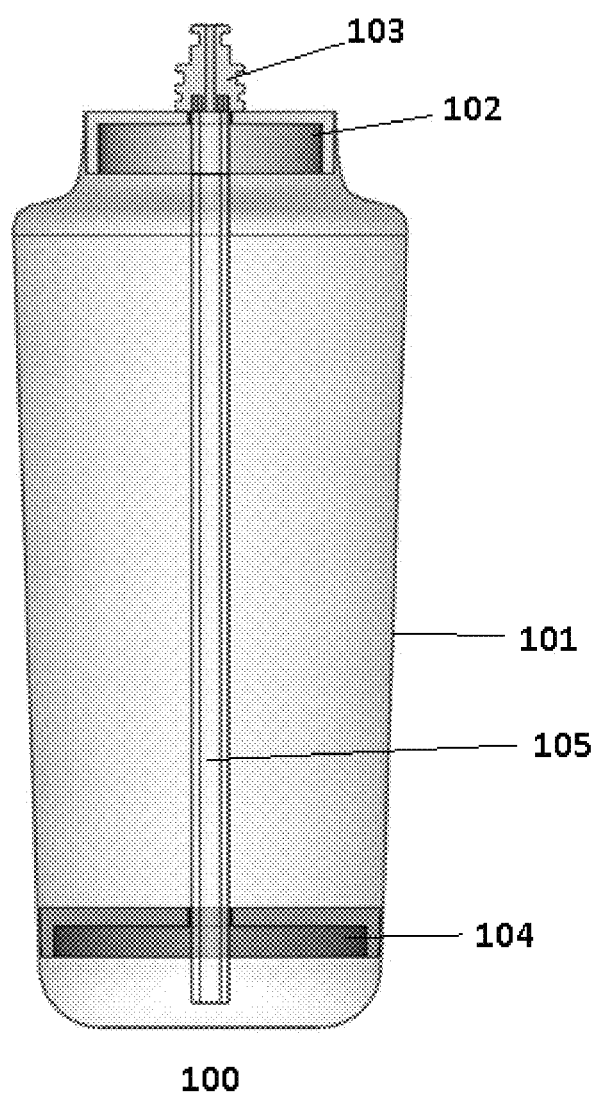
FIG. 1 shows a flexible infusate sleeve with for use in dialysis.

Unless defined otherwise, all technical and scientific terms used herein generally have the same meaning as commonly understood by one of ordinary skill in the relevant art.

The articles "a" and "an" are used to refer to one or to over one (i.e., to at least one) of the grammatical object of the article. For example, "an element" means one element or over one element.

The term "bi-channel connector" refers to a fluid connector having two channels for fluid movement in either direction.

The term "bottom portion" of a container refers to the portion of the container or component near or at a lowest elevation.

The term "cap" refers to a portion of a component covering an opening.

The term "cation infusate" refers to cations that are added to a dialysate during dialysis therapy.

The term "channel" refers to any pathway within a component through which a fluid may travel.

The term "comprising" includes, but is not limited to, whatever follows the word "comprising." Use of the term indicates the listed elements are required or mandatory but that other elements are optional and may be present.

The terms "connect" or "connected" refer to a physical contact that resists movement between two or more components. The connections can be detachable and reattached between the two or more components.

The term "consisting of" includes and is limited to whatever follows the phrase "consisting of" The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "cup" refers to a component having a base and upwardly extending sidewalls defining an interior space.

A "dialysate flow path" is a route in which a fluid can travel during dialysis.

"Dialysis" or "dialysis therapy" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

A "dialysis system" is a system comprising a dialyzer, pumps, valves and fluid lines that is used to carry out a dialysis session.

A "disk" is a planar component having a substantially round or circular shape.

The terms "dissolving" or to "dissolve" refer to causing a solid or gas to become incorporated into a liquid to form a solution.

"Downwardly extending" or to "extend downwardly" refers to a component positioned from a higher elevation to a lower elevation A "draw tube" is a fluid connector extending into an interior space of a component.

A "filter" is a component that inhibits the passage particulate matter conveyed by a fluid or solution while allowing the passage of the fluid or solution.

The term "flexible" refers to a component having a shape that can be changed or bent.

The terms "flowing" or to "flow" "refer to the movement of" a fluid, gas, or mixtures thereof.

A "fluid" is a liquid substance optionally having a combination of gas and liquid phases in the fluid. Notably, a liquid can therefore also have a mixture of gas and liquid phases of matter.

The term "fluid connector," "fluidly connectable," or "fluidly connected" refers to the ability to pass fluid, gas, or mixtures thereof from one point to another point. The two points can be within or between any one or more of compartments, modules, systems, and components, all of any type.

The term "fluid line" refers to a fluid pathway.

The term "fluid pump" or "pump" refers to any device that causes the movement of fluids or gases by applying suction or pressure.

The term "frit filter" refers to porous glass made by sintering together glass particles into a porous body.

The term "heat sealing" or "heat sealed" refers to the use of heat to unite or connect two thermoplastic materials.

An "infusate container" is a container adapted to contain one or more fluids for use in dialysis. The infusate container can at times hold dry chemicals that are later able to be reconstituted with a fluid to form a further useable fluid within the system.

The term "infusate container body" refers to the outer boundaries of a container enclosing the interior of the infusate container.

An "infusate sleeve" is a disposable component insertable into an infusate container into which the infusate is placed.

An "infusate solution" is any substance or substances dissolved in water or dialysate to be added to a dialysate flow path.

The term "mesh" refers to a component made of strands of fibers with spaces between the fibers to allow fluid or gas to flow through the mesh.

An "opening" is a portion of a component having a defined void space.

The term "outside" refers to the portion of a component on the exterior of the component.

The term "rigid" refers to a component having a substantially stiff structure that resist bending and is not generally flexible.

The term "saturated" refers to the highest amount of a substance that can be dissolved in a solvent at a given temperature.

The term "sealed" refers to a connection between two components through which a fluid, gas, and mixtures thereof cannot pass.

The term "sleeve body" refers to the outer boundaries of a container enclosing an interior of a container.

The term "solid infusate" refers to any substance intended to be added to a dialysate flow path in the solid form of matter.

The term "top portion" of a container refers to the portion of the container or component near or at a highest elevation.

Infusate Sleeve

FIG. 1 illustrates a non-limiting embodiment of an infusate sleeve 100. The infusate sleeve 100 can be a flexible material into which infusates for use with a dialysis system can be placed. The infusate sleeve 100 has a sleeve body 101 with an opening in the top portion of the sleeve body 101. A rigid disk 102 can be sealed to the top portion of the sleeve body 101, covering the opening. The rigid disk 102 can have a fluid connector 103 connected to the outside of the rigid disk 102 for fluidly connecting to one or more fluid lines in a dialysis system. The fluid connector 103 can connect to a draw tube 105 through which an infusate solution can be drawn out of the infusate sleeve 100 and into the dialysis system. A pump connected to the fluid line can provide the driving force for the movement of fluid into and out of the infusate sleeve 100 through fluid connector 103.

The rigid disk 102 provides a stable top for the infusate sleeve 100, allowing easier connection of the fluid connector 103 to a dialysis system. The rigid disk 102 can be sealed to the sleeve body 101 of the infusate sleeve 100 by any means known in the art that can create a seal, including heat sealing, molding, gluing, soldering, and mechanical fixation. The infusate sleeve 100 also includes a filter 104 sealed to the sleeve body 101. The filter 104 separates the infusate sleeve 100 into a top portion and a bottom portion. A solid infusate can be placed on top of the filter 104. Water can be into the infusate sleeve 100 to dissolve the infusate with the resulting solution flowing below the filter 104 into the bottom portion. The solids cannot pass through the filter 104, and remain in the top portion. The filter 104 can be any type of filter known in the art capable of preventing solid or particulate matter from passing through the filter 104, including a frit filter or a mesh filter. The filter 104 can be sealed to the sleeve body 101 by any method known in the art capable of creating a seal between the sleeve body 101 and the filter 104, including heat sealing. The draw tube 105 can extend downwardly from the rigid disk 102 through the filter 104. The solution in the bottom portion of the infusate sleeve 100 can be drawn through the draw tube 105 and added to a dialysate flow path with a pump positioned on a fluid line connected to the draw tube 105.

Figure 2:
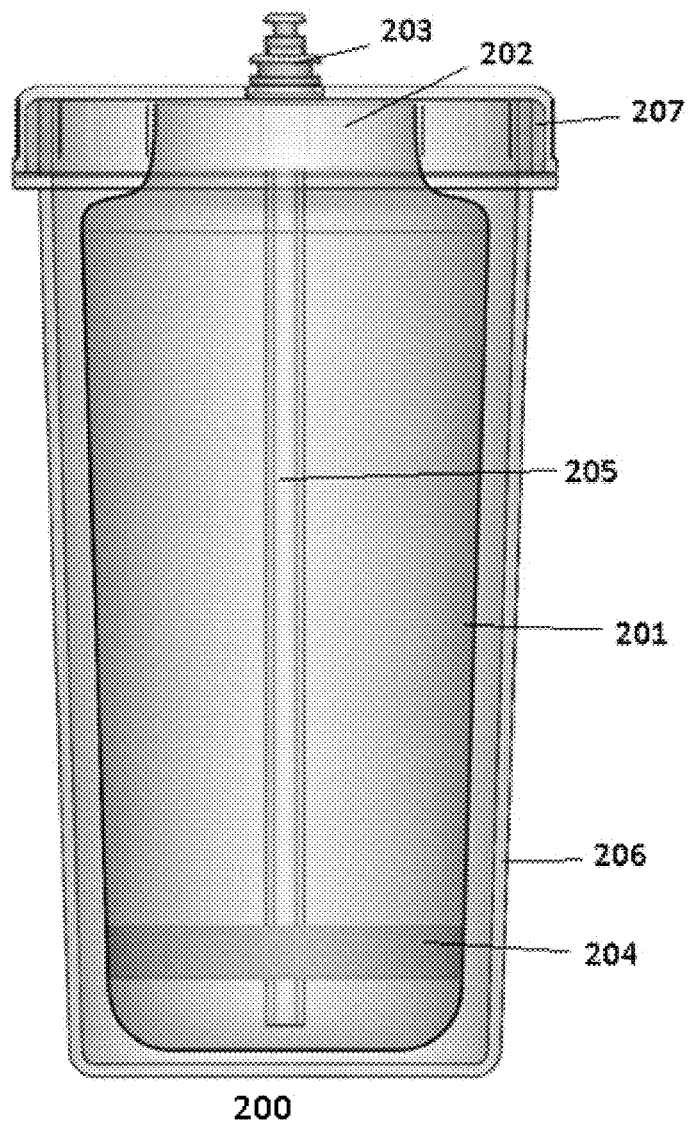
FIG. 2 shows a flexible infusate sleeve inside of an infusate container.

For use with a dialysis system, the infusate sleeve 201 can be inserted into an infusate container 200 as illustrated in FIG. 2. The infusate sleeve 201 can be inserted into the infusate container 200. The infusate container 200 has a rigid infusate container body 206 that provides a stable and rigid structure, allowing the fluid connector 203 to be easily connected to and disconnected by transferring the force when connecting from the flexible infusate sleeve 201 to the dialysis system. The infusate sleeve 201 can include a rigid disk 202 with a fluid connector 203 on the outside of the rigid disk 202 connected to a draw tube 205. A filter 204 prevents solid or particulate matter from being added to a dialysate flow path through draw tube 205. The rigid disk 202 can engage with a cap 207 on the infusate container 200. The cap 207 can have an opening through which the fluid connector 203 can extend for connection to the dialysis system.

The infusate sleeve 201 can be a disposable part, while the infusate container 200 is reusable. The infusate sleeve 201 thus allows a cheap method to contain and use infusates, while eliminating the need for cleaning and sterilization of the infusate container 200. For each dialysis session, the user need only insert a new infusate sleeve 201 into the reusable infusate container 200. After placing a solid infusate into the infusate sleeve 201 above the filter 204, purified water from the dialysis system can be added to the infusate sleeve 201 to dissolve the solid infusate, creating an infusate solution that flows through the filter 204 into the bottom portion of the infusate sleeve 201. The infusate sleeve 201 expands upon filling with water to accommodate the larger volume within the infusate sleeve 201. For use with solid infusates, water can be added to the infusate sleeve 201 to dissolve the infusate, making a solution of known concentration for addition to a dialysis system. For example, an excess amount of the solid infusate can be added to the infusate sleeve 201. Water can be added to the infusate sleeve 201 in an amount insufficient to dissolve all of the solid infusate. The resulting infusate solution will be saturated in the infusate. At known temperatures, the concentration of the infusate in the saturated infusate solution will be known. Alternatively, a specified amount of solid infusate and water can be added to the infusate sleeve 201 to generate an infusate solution of known concentration.

Figure 3:
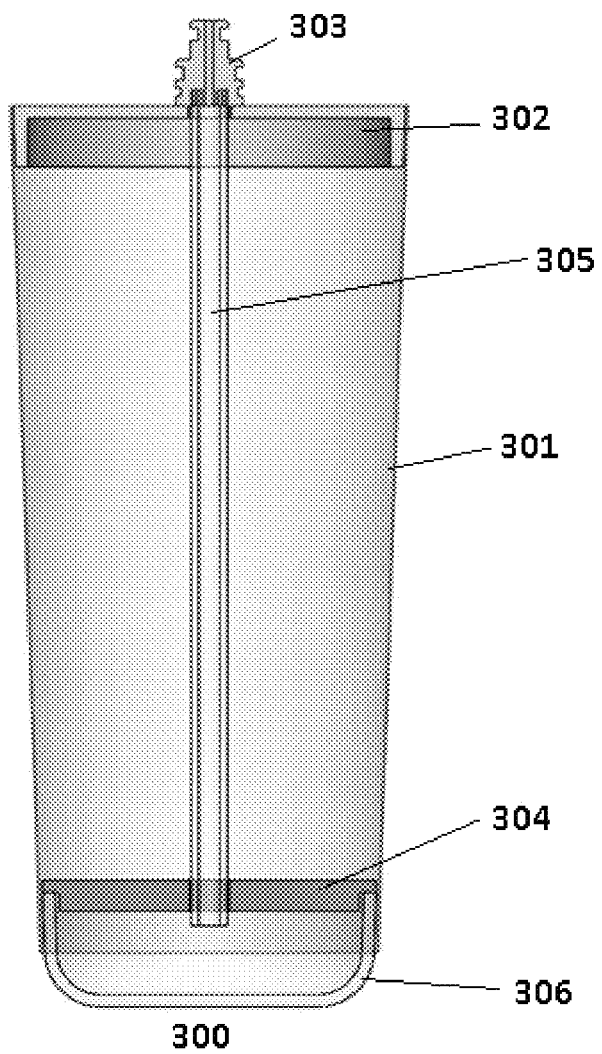
FIG. 3 shows a rigid infusate sleeve for use in dialysis.

FIG. 3 illustrates an alternative infusate sleeve 300 with openings in the top and bottom of the sleeve body 301. As with the infusate sleeve 100 illustrated in FIG. 1, the infusate sleeve 300 in FIG. 3 has an opening in the top portion of the sleeve body 301. A rigid disk 302 can be sealed to the top portion of the sleeve body 301, covering the opening. The rigid disk 302 can have a fluid connector 303 for connection to one or more fluid lines in a dialysis system. The fluid connector 303 can connect to a draw tube 305 through which an infusate solution can be drawn out of the infusate sleeve 300 and into the dialysis system. A pump connected to the fluid line can provide the driving force for the movement of fluid into and out of the infusate sleeve 300 through fluid connector 303. The infusate sleeve 300 also has an opening in the bottom portion of the sleeve body 301. A cup 306 can cover the opening in the bottom portion of the sleeve body 301 and can be sealed to the sleeve body 301 by any means known in the art. The cup 306 is a rigid component that, with the rigid disk 302, maintains the shape of the infusate sleeve 300. A filter 304 can be sealed to the infusate sleeve 300 and sit on top of the cup 306. The infusate sleeve 300 can be a rigid component to further maintain the shape of the infusate sleeve 300. By using a rigid infusate sleeve 300 pressure buildup due to addition of water into the infusate sleeve 300 can be eliminated.

Figure 4:
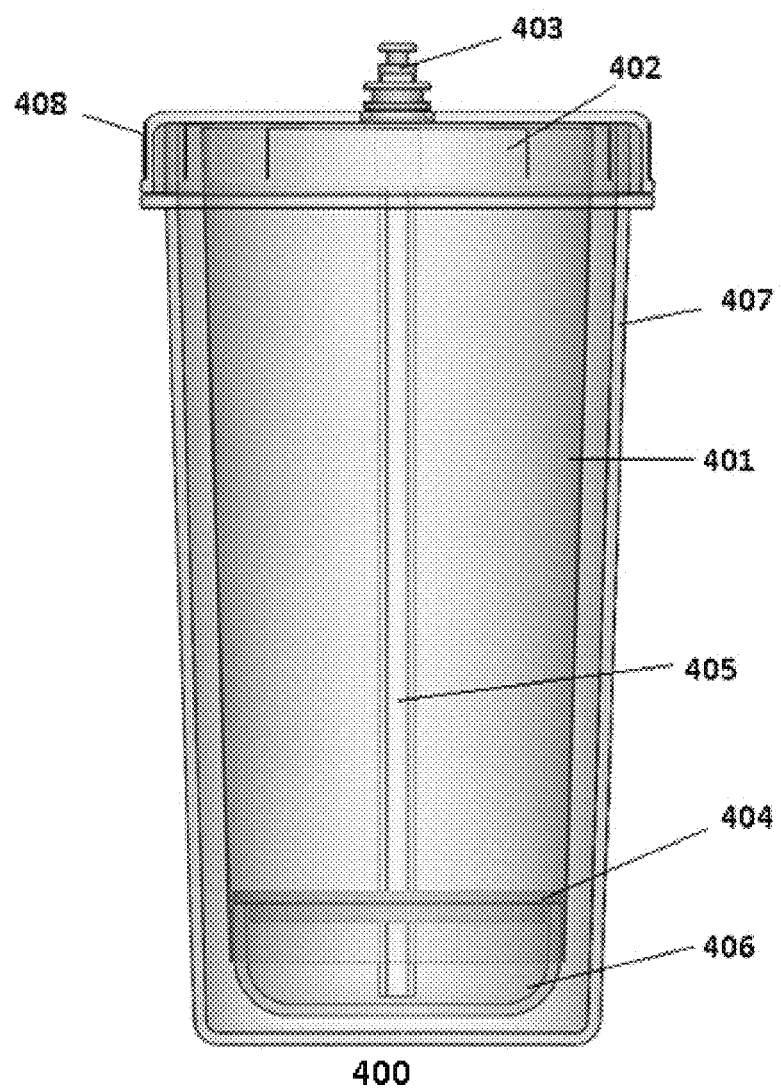
FIG. 4 shows a rigid infusate sleeve inside of an infusate container.

FIG. 4 illustrates an infusate sleeve 401 as illustrated in FIG. 3 inside of an infusate container 400. The infusate sleeve 401 can be inserted into the infusate container 400. The infusate container 400 has a rigid infusate container body 407 that provides a stable and rigid structure, allowing the fluid connector 403 to be easily connected to and disconnected by transferring the force when connecting from the infusate sleeve 401 to the dialysis system. The infusate sleeve 401 can include a rigid disk 402 with a fluid connector 403 connected to a draw tube 405. A filter 404 prevents solid or particulate matter from being added to a dialysate flow path through draw tube 405. The rigid disk 402 can engage with a cap 408 on the infusate container 400. The cap 408 can have an opening through which the fluid connector 403 can extend for connection to the dialysis system. The cup 406 can sit on top of a base of the infusate container 400. Because the rigid disk 402 and cup 406 hold the infusate sleeve 401 in shape, the infusate sleeve 401 does not need to expand when water is added to the infusate sleeve 401. Instead, the infusate sleeve 401 fills the infusate container 400, eliminating the buildup of pressure in the infusate sleeve 401 as fluid is added to the infusate sleeve 401. By eliminating the pressure buildup, inadvertent popping of the infusate sleeve 401 can be avoided.

The infusate sleeves can be used with any infusate necessary for priming, disinfecting, or providing treatment with a dialysis system. The infusate sleeves can contain sodium bicarbonate, sodium chloride, cation infusates, or combinations thereof. Any number of infusate sleeves and infusate containers can be used with a dialysis system, including 1, 2, 3, 4, 5, or more. A single cation infusate sleeve can be used for all cation infusates, or separate cation infusate sleeves can be used for each cation to be added to a dialysate flow path, such as potassium, magnesium, and calcium.

Figure 5A:
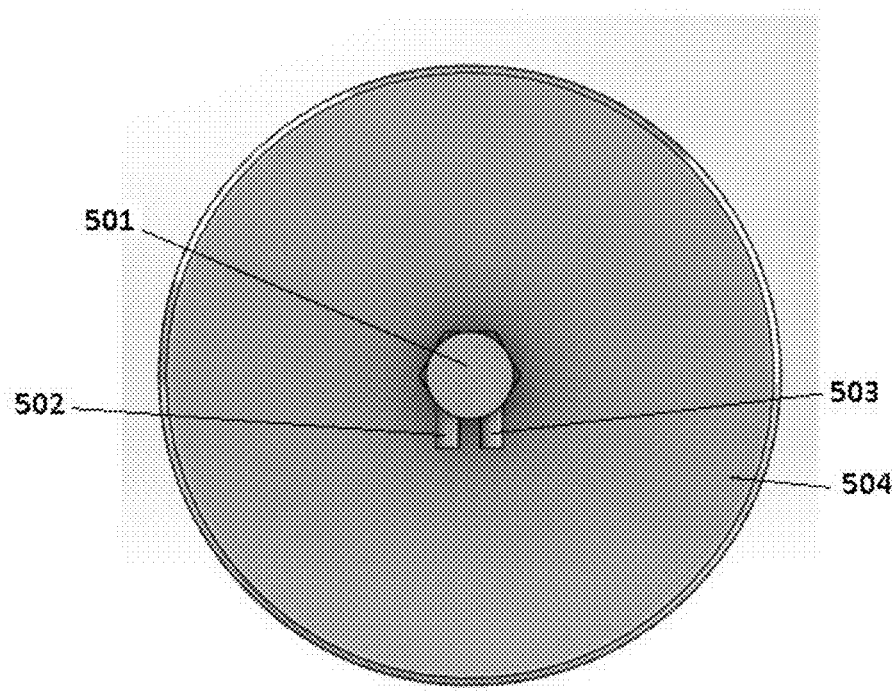
FIGS. 5A-D show bi-channel connectors for use with the infusate sleeve.
Figure 5B:
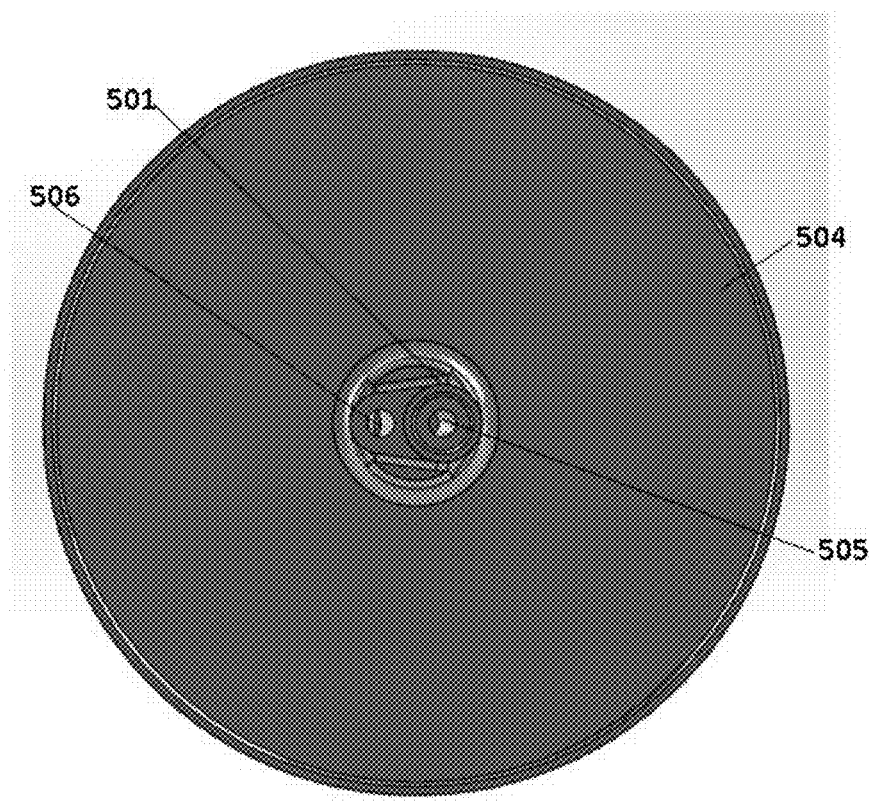
Figure 5C:
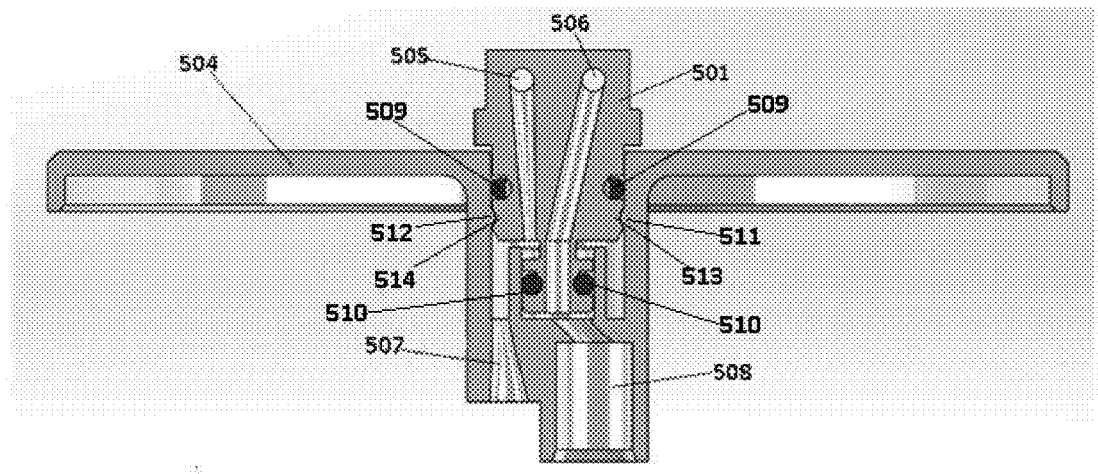
Figure 5D:
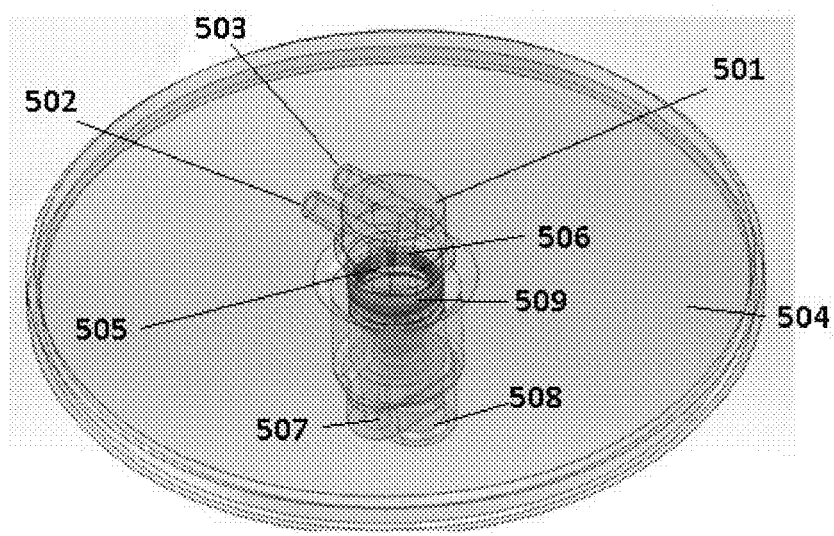

Any of the fluid connectors described can be bi-channel connectors. FIGS. 5A-D illustrate one embodiment of a bi-channel connector 501. FIG. 5A is a top view of a bi-channel connector 501, FIG. 5B is a top cut-away view of the bi-channel connector 501, FIG. 5C is a cross-sectional view of the bi-channel connector 501, and FIG. 5D is a transparent view of the bi-channel connector 501. Each view shows a rigid disk 504 and bi-channel connector 501. The connector 501 includes fluid inlet 502 for moving fluid into the infusate sleeve (not shown in FIGS. 5A-D), and fluid outlet 503 for removing fluid from the infusate sleeve. The fluid inlet 502 is connected to a first channel 505, and the fluid outlet 503 is connected to a second channel 506, as illustrated in FIG. 5B. The first channel 505 is connected to an infusate sleeve inlet 507 for movement of fluid into the infusate sleeve. The second channel 506 is connected to an infuse sleeve outlet 508 for movement of fluid out of the infusate sleeve. The infuse sleeve outlet 508 can be fluidly connected to a draw tube (not shown in FIGS. 5A-D) that extends downwardly into the container body. An o-ring or other sealing member 509 can be included to prevent leakage around the rigid disk 504 of the infusate sleeve where the rigid disk 504 contacts the bi-channel connector 501. As illustrated in FIG. 5C, a second o-ring 510 can be included to prevent leakage between the first channel 505 and second channel 506. The rigid disk 504 can also include protrusions 511 and 512 which can engage with complementary indentations 513 and 514 on the bi-channel connector 501 to securely fasten the bi-channel connector 501 in place on the rigid disk 504 without the need to twist or screw the bi-channel connector 501

The fluid inlet 502 and fluid outlet 503 can be fluidly connected to a dialysis system through separate fluid lines. By using separate fluid lines for influx and efflux of fluid to and from the infusate sleeve, additional water can be added to the infusate sleeve during priming or use without contamination of the infusates within the container.

Figure 6A:
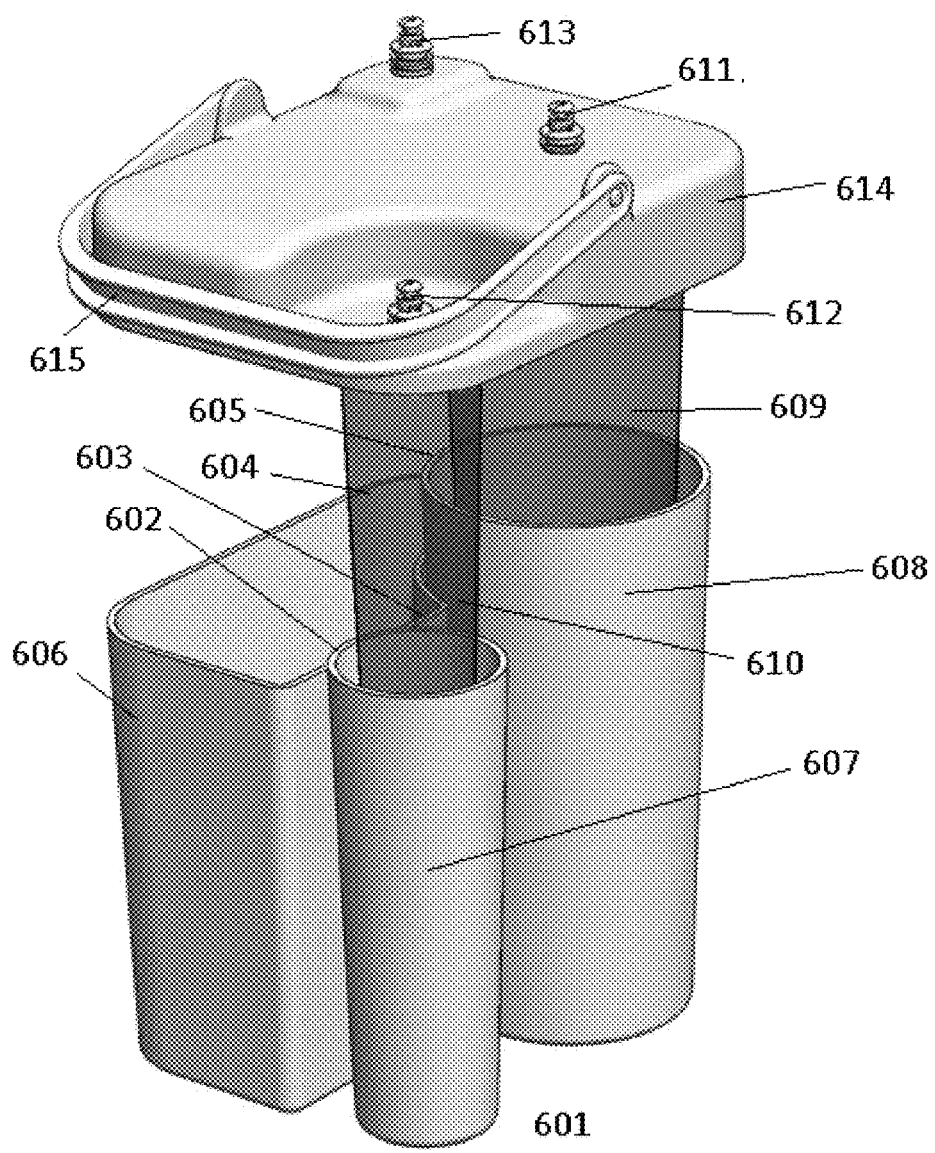
FIGS. 6A-C show an infusate holder for use with integrally formed disposable infusate sleeves.
Figure 6B:
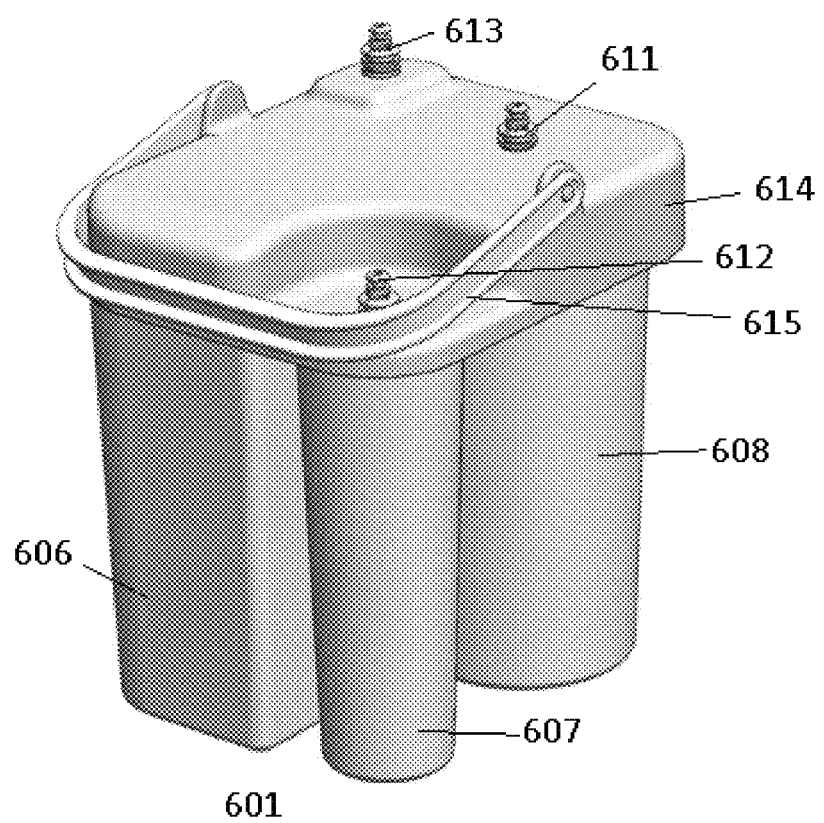
Figure 6C:
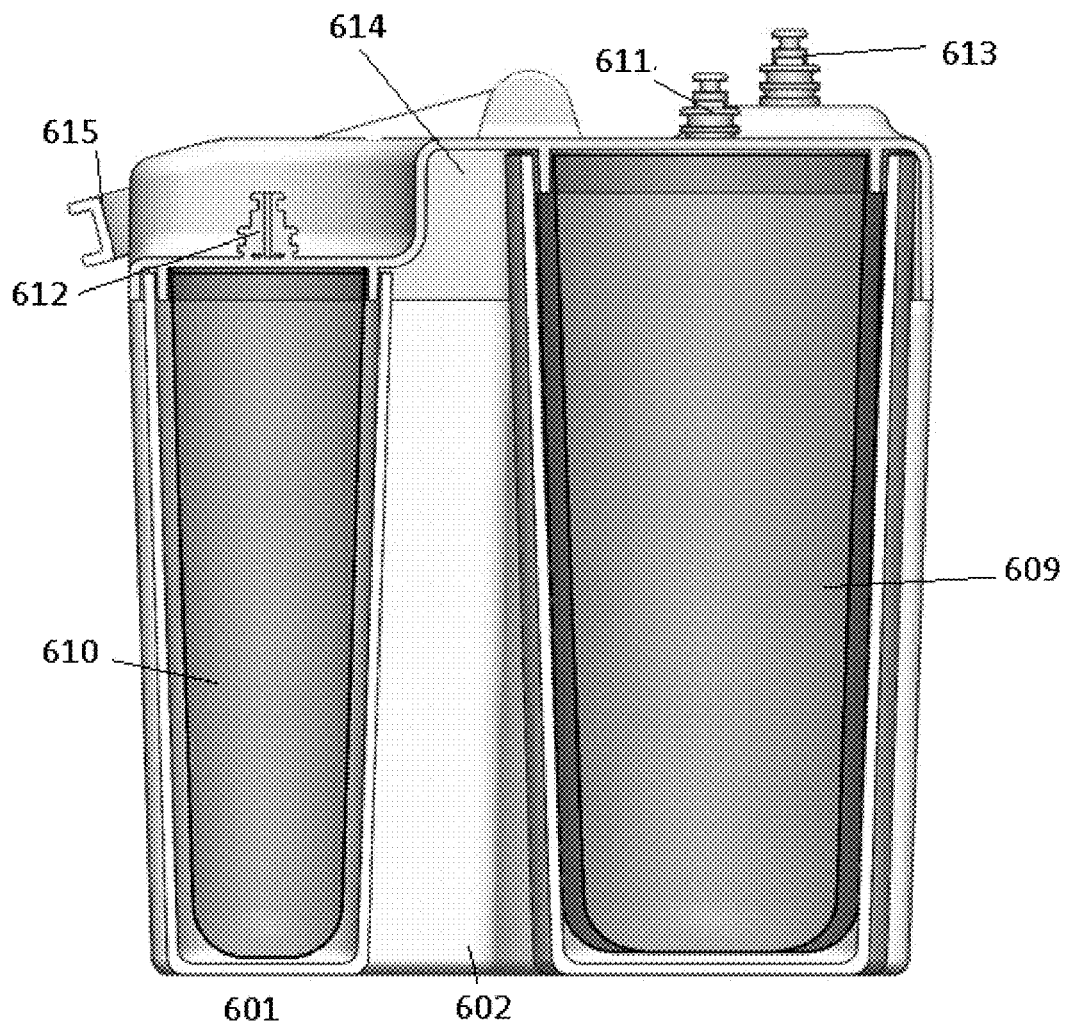

FIGS. 6A-C illustrate an infusate holder 601 with a disposable lid 614 integrally formed with disposable sodium bicarbonate infusate sleeve 609 and sodium chloride infusate sleeve 610. Additional disposable or reusable infusate sleeves (not shown) can be included in the infusate holder 601. FIG. 6A illustrates the infusate holder 601 with the lid 614 detached, FIG. 6B illustrates the infusate holder 601 after attaching the lid 614, and FIG. 6C is a cutaway view of the infusate holder 601 after attaching the lid 614. Upwardly extending interior walls 602, 603, 604, and 605 define interior compartment 608 for holding a sodium bicarbonate infusate sleeve 609, interior compartment 607 for holding a sodium chloride infusate sleeve 610, and interior compartment 606 for holding an additional infusate sleeve or infusate container (not shown). The sodium bicarbonate infusate sleeve 609 and sodium chloride infusate sleeve 610 can be integrally formed with the lid 614. The lid 614 performs the same functions as the rigid disks described with reference to FIGS. 1-5. When the lid 614 is placed on the infusate holder 601, as illustrated in FIG. 6B, the sodium bicarbonate infusate sleeve 609 and sodium chloride infusate sleeve 610 are placed within interior compartments 608 and 607 respectively. Fluid connector 611 provides for fluid ingress and egress from sodium bicarbonate infusate sleeve 609, and fluid connector 612 provides for fluid ingress and egress from sodium chloride infusate sleeve 610. Fluid connector 613 can connect to a disposable or non-disposable cation infusate container (not shown). Handle 615 can be included for easy maneuverability of the infusate holder 601.

To use the disposable sodium chloride infusate sleeve 610 and sodium bicarbonate infusate sleeve 609, fluid from a dialysate flow path (not shown) is added to solid infusate sources within the infusate sleeve. The addition of fluid from the dialysate flow path pressurizes the infusate sleeves. The interior and exterior walls of interior compartments 606, 607, and 608 provide support for the pressurized flexible infusate sleeves, preventing the infusate sleeves from tearing during use, as illustrated in FIG. 6C. The interior compartment 608 and disposable sodium bicarbonate infusate sleeve 609 can each have a tapered bottom portion (not shown in FIGS. 6A-C) to increase efficiency of sodium bicarbonate delivery. A tapered bottom portion of the sodium bicarbonate infusate sleeve 609 increases delivery efficiency of sodium bicarbonate from the sodium bicarbonate sleeve 609 from about 50% to over 90% as compared to a sodium bicarbonate infusate sleeve 609 without a tapered bottom portion.

Figure 7A:
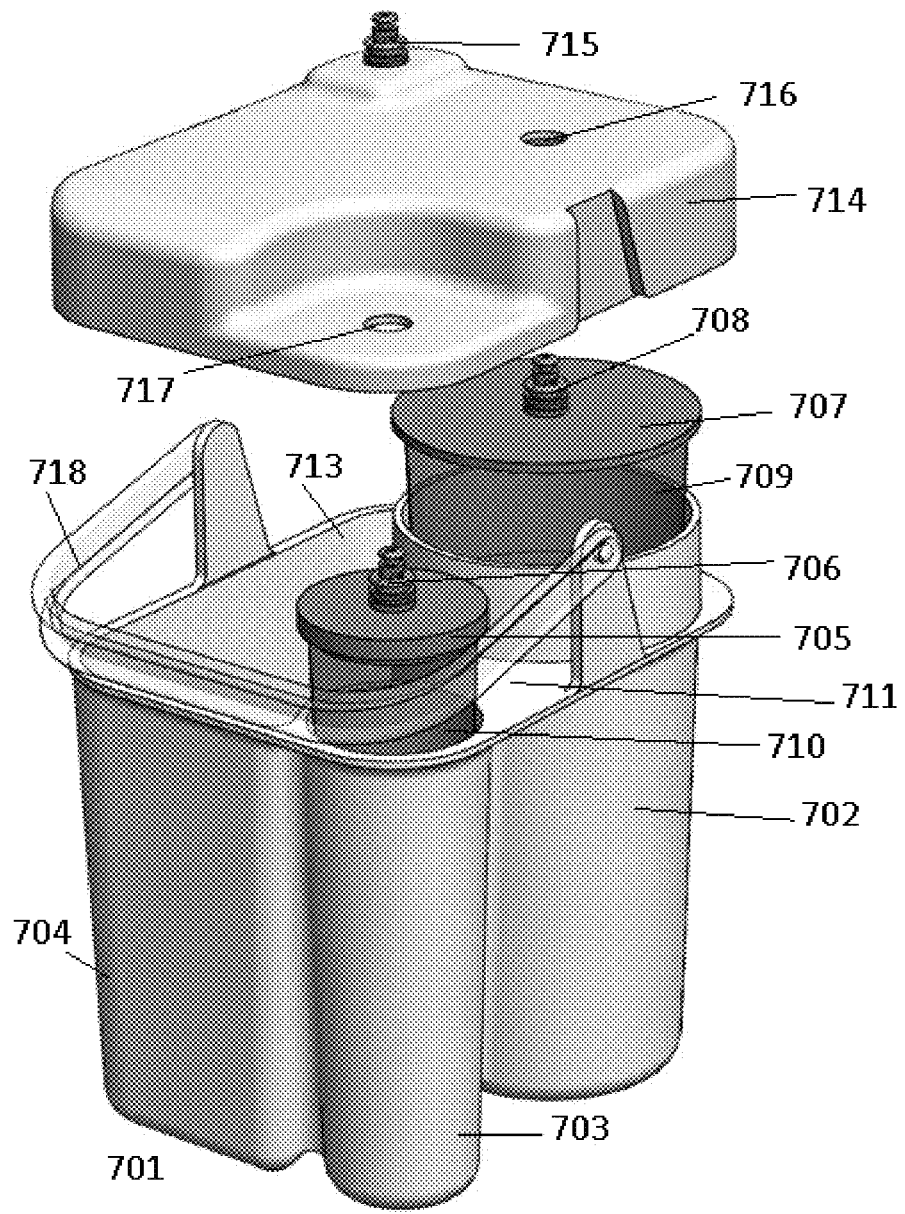
FIGS. 7A-B show an infusate holder for use with separate disposable infusate sleeves.
Figure 7B:
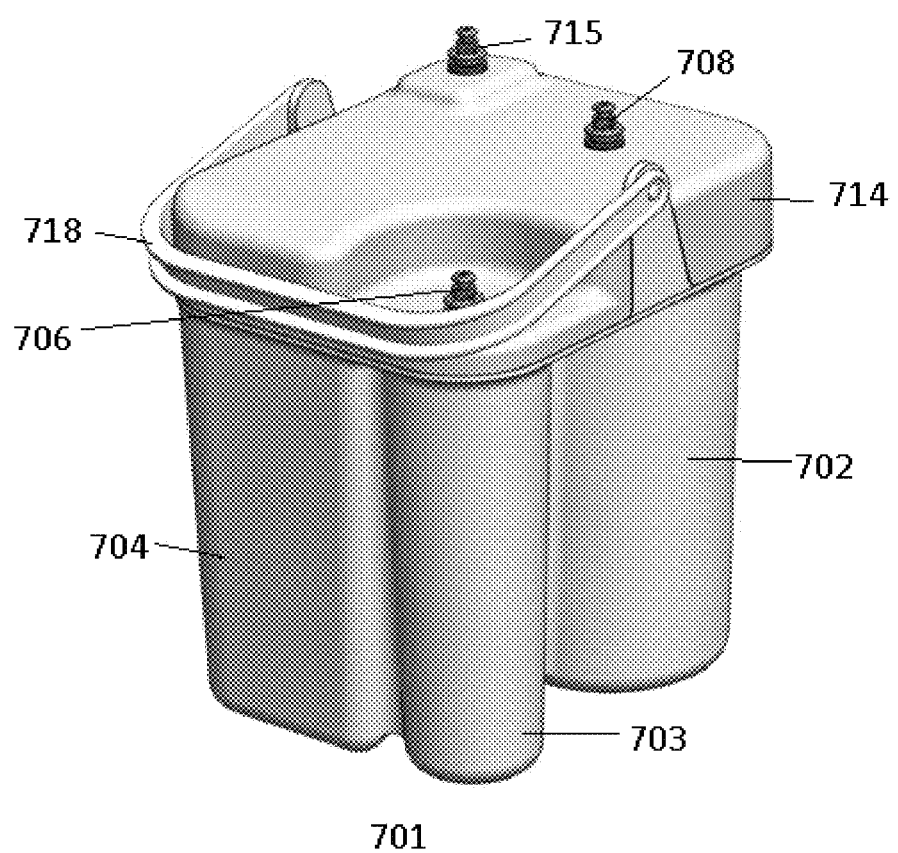

FIGS. 7A-B illustrate an infusate holder 701 with a reusable lid 714 formed separately from disposable sodium bicarbonate infusate sleeve 709 and sodium chloride infusate sleeve 710. FIG. 7A illustrates the infusate holder 701 with the lid 714 detached, and FIG. 7B illustrates the infusate holder 701 after attaching the lid 714. The disposable sodium bicarbonate infusate sleeve 709 and sodium chloride infusate sleeve 710 can be integrally formed with or attached to rigid disks 707 and 705, respectively. The rigid disks 707 and 705 can include connectors 708 and 706 for connection to a dialysis system. Exterior walls 702, 703 and 704, as well as interior wall 711 can form an interior compartment for the sodium bicarbonate infusate sleeve 709 and sodium chloride infusate sleeve 710, as well as one or more additional interior compartments 713 for additional infusate sleeves (not shown). The lid 714 can include opening 716 for insertion of connector 708 and opening 717 for connector 706. The openings 716 and 717 are aligned with the interior compartments for insertion of the connectors 708 and 706. An additional connector 715 can be included in the lid 714 for connection to a cation infusate sleeve or other infusate sleeve (not shown). Alternatively, the other infusate sleeve can include a connector, and a third opening can be included in the lid 714 in place of connector 715. Handle 718 can be included for easy maneuverability of the infusate holder 701.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:

1. An infusate sleeve, comprising:
a sleeve body;
a filter inside of the sleeve body and sealed to the sleeve body separating the sleeve body into a top portion and a bottom portion;
a rigid disk sealed to the top portion of the sleeve body; the rigid disk covering an opening in the top portion of the sleeve body;
a second opening in the bottom portion of the sleeve body;
a draw tube connected to the rigid disk; the draw tube downwardly extending from the rigid disk through the filter and into the bottom portion; and
a fluid connector connected to an outside of the rigid disk; the fluid connector in fluid connection with the draw tube.

2. The infusate sleeve of claim 1, wherein the filter and rigid disk are heat sealed to the sleeve body.

3. The infusate sleeve of claim 1, wherein the sleeve body is flexible.

4. The infusate sleeve of claim 1, wherein the sleeve body is rigid.

5. The infusate sleeve of claim 1, wherein the fluid connector is a bi-channel connector.

6. The infusate sleeve of claim 5, wherein a first channel in the bi-channel connector is fluidly connected to the draw tube.

7. The infusate sleeve of claim 1, further comprising a cup covering the opening in the bottom portion of the sleeve body; the cup sealed to the sleeve body.

8. The infusate sleeve of claim 7, wherein the filter is sealed to the cup.

9. The infusate sleeve of claim 1, wherein the filter is either a mesh or frit filter.

10. An infusate container, comprising:
an infusate container body;
the infusate sleeve of claim 1 inside the container body; and
a cap; wherein the fluid connector extends through an opening in the cap.

11. The infusate container of claim 10, wherein the infusate sleeve is flexible.

12. The infusate container of claim 10, wherein the infusate sleeve is rigid.

13. A method, comprising the steps of:
flowing water into the infusate container of claim 10, wherein the infusate container contains a solid infusate;
dissolving at least a portion of the solid infusate to make an infusate solution; and
flowing the infusate solution into a dialysate flow path.

14. The method of claim 13, wherein the step of flowing water into the infusate container comprises flowing water through a first channel of a bi-channel connector; and wherein the step of flowing the infusate solution into the dialysate flow path comprises flowing the infusate solution through a second channel of the bi-channel connector.

15. The method of claim 13, wherein the step of dissolving at least a portion of the solid infusate to make an infusate solution comprises making a saturated infusate solution.

16. The method of claim 13, wherein the solid infusate is sodium bicarbonate, sodium chloride, a cation infusate, or a combination thereof.

17. A dialysis system, comprising:
a dialysate flow path;
one or more fluid connectors fluidly connecting one or more infusate containers to the dialysate flow path;
wherein the one or more infusate containers comprise an infusate container body, the infusate sleeve of claim 1 inside the container body, and a cap; wherein the one or more fluid connectors extends through an opening in the cap;
at least one pump connected to a fluid line fluidly connected to the one or more fluid connectors.

18. The dialysis system of claim 17, wherein the one or more fluid connectors are bi-channel connectors.

19. The dialysis system of claim 18, wherein a first channel of the bi-channel connector fluidly connects the draw tube to a first fluid line; and wherein a second channel of the bi-channel connector fluidly connects the infusate sleeve to a second fluid line.

20. The dialysis system of claim 17, wherein the infusate sleeve contains sodium chloride, sodium bicarbonate, a cation infusate, or combinations thereof.

* * * * *